United States Patent
Poore et al.

(10) Patent No.: US 7,103,414 B1
(45) Date of Patent: Sep. 5, 2006

(54) COMBINED PROGRAMMING WAND AND PSA FOR PACEMAKER AND ICD PROGRAMMER SYSTEM

(75) Inventors: John W. Poore, South Pasadena, CA (US); Eric Falkenberg, Simi Valley, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 70 days.

(21) Appl. No.: 10/829,907

(22) Filed: Apr. 21, 2004

(51) Int. Cl.
*A61N 1/18* (2006.01)
*A61N 1/372* (2006.01)

(52) U.S. Cl. .............................. 607/32; 607/27; 607/30; 607/60

(58) Field of Classification Search .................. 607/30, 607/32, 59, 60, 27
See application file for complete search history.

(56) References Cited

U.S. PATENT DOCUMENTS

| | | | | |
|---|---|---|---|---|
| 4,809,697 A | * | 3/1989 | Causey et al. ................ | 607/31 |
| 5,311,449 A | | 5/1994 | Adams ........................ | 364/514 |
| 5,383,915 A | * | 1/1995 | Adams ........................ | 607/60 |
| 5,679,022 A | * | 10/1997 | Cappa et al. ................ | 439/502 |
| 5,759,199 A | * | 6/1998 | Snell et al. ................... | 607/60 |
| 2001/0037220 A1 | | 11/2001 | Merry et al. ................... | 705/3 |
| 2002/0007198 A1 | | 1/2002 | Haupert et al. ............... | 607/30 |

FOREIGN PATENT DOCUMENTS

| WO | WO 01/47410 A2 | 7/2001 |
|---|---|---|
| WO | WO 01/47410 A3 | 7/2001 |
| WO | WO 01/ 87413 A1 | 11/2001 |

* cited by examiner

*Primary Examiner*—Robert E. Pezzuto
*Assistant Examiner*—Jessica L. Reidel

(57) ABSTRACT

A combined programming wand and PSA for physician programmers. A programmer/PSA wand can be connected to known programmers and PSA application software can be installed on the programmer to provide a system with the functionality of a PSA and a programmer in a single piece of clinical equipment. The programmer/PSA wand includes electronics to sense, pace, and shock to facilitate evaluation of indwelling leads during implantation of the implantable device and leads to facilitate programming of the device. The system includes one or more displays and control inputs that can provide information to a clinician at a single point that is typically provided with separate programmer and PSA equipment. The system provides increased efficiency, reduced opportunities for errors and/or equipment malfunction, and integrated data collection.

19 Claims, 14 Drawing Sheets

COMBINED PROGRAMMING WAND AND PSA FOR PACEMAKER AND ICD PROGRAMMER SYSTEM

FIELD OF THE INVENTION

The invention relates to the field of implantable medical devices and, in particular, to a programming wand for a physician programmer with integral PSA functionality.

BACKGROUND OF THE INVENTION

Implantable cardiac stimulation devices, such as pacemakers and implantable cardioverter-defibrillators (ICDs), typically include a pulse generator that includes circuitry for detecting cardiac arrhythmias and automatically generating and delivering therapeutic electrical stimulations to the patient's heart via one or more indwelling leads. The leads include one or more electrodes that are positioned and secured adjacent to excitable heart cells and an insulated electrical conductor that allows stimulation pulses from the pulse generator to be passed to the electrode(s) and thus to the heart tissue.

The implantation procedure for implantable cardiac stimulation devices involves placement of one or more of the leads in an operating room (O.R.) or electrophysiology (EP) catheter lab. In particular, the lead(s) are positioned and secured in contact with the patient's heart both to sense cardiac activity for detection of possible arrhythmic conditions indicating therapeutic stimulation as well as to provide a circuit for delivery of indicated stimulation pulses. The implantation procedure involves confirmation of the proper placement of the lead(s) as well as the electrical conductivity of the lead circuit(s) and the integrity of the insulation surrounding the conductive elements.

The implantation procedure also includes establishing a variety of electrical characteristics of the circuit between the pulse generator and the cardiac tissue. The electrical characteristics of the circuit(s) between the pulse generator and the heart as well as the characteristics of the heart tissue itself affect sensing of cardiac signals and delivery of electrical stimulation provided by the pulse generator and thus, the signal sensing quality, and the threshold stimulation that must be provided to effectively induce depolarization of the heart. These characteristics include the electrical conductivity of the conductor between the pulse generator and the electrode; the conductivity, surface area, and configuration of the electrode; and the contact between the electrode and the excitable heart tissue.

It is generally desirable to stimulate the heart, when indicated, with a stimulation pulse minimally in excess of a minimum required to effect depolarization. However as effective detection and stimulation are required after implant and, as individual characteristics and requirements vary, many operating parameters of the implantable device relating to arrhythmia detection and stimulation delivery are programmable to provide individually tailored device performance. The determined sensing and stimulation values are used to program operating parameters of the implantable device.

A device often used in the implantation process to test and evaluate the lead integrity, sensing, and stimulation is referred to as a pacing system analyzer (PSA). The PSA is typically only used during an implantation procedure and operates as a pulse generator whose operational parameters are variable. The PSA functions as a surrogate for the implantable device to evaluate the performance of the lead(s) themselves, sensing, and pacing. The characteristics of the sensing and stimulation determined with the aid of the PSA then helps determine the programming of the implantable device.

The initial implantation as well as ongoing clinical care provided to patients with implantable cardiac device systems also generally includes the use of physician programmers. A programmer is a device that enables a clinician to telemetrically communicate with and control an implantable cardiac device such as a pacemaker or ICD. Implantable devices are generally capable of receiving telemetric signals from a programmer to induce the device to set or change a variety of operational parameters of the device related to the therapy provided by the device as well as to select among the physiological parameters that the device monitors and records. As mentioned, these parameters are typically programmed into the device specifically for an individual patient. Data determined following fixation of the lead(s) and with use of a PSA generally is used to determine appropriate programming for the individual patient.

As patient condition can vary over time and improved operating algorithms become available, the parameters are also often desirably changed following the initial implantation to adjust the therapy provided and/or the physiological parameters monitored in order to provide the attending clinician with different information or to adapt the therapy to a more efficacious regimen. It is highly desirable to set these parameters without the expense and health risks to the patient of additional invasive procedures and programmers enable the attending clinician to perform these tasks in a non-invasive, telemetric manner after implantation with the insight of information provided from internal measurements provided by the device itself.

Implantable devices generally monitor and record a variety of internal physiological parameters of the patient and are often provided with a telemetry system to telemetrically transmit those measured and recorded parameters outside the patient's body to a programmer. The implantable devices can also transmit to the programmer data related to present device status, such as programmed operational parameters, battery capacity state, therapy provided and cardiac conditions observed, etc. A clinician can then review the data via the programmer and make any indicated changes in the patient's therapy.

Accordingly, programmers typically include a display to visually present alphanumeric and graphical information relating to device performance and patient condition as well as user input devices to facilitate data entry and control inputs to be provided by a clinician to control device operation telemetrically. As implantable devices are typically battery powered, thus having limited electrical power capacity and, as telemetric communication can be a relatively major source of battery depletion, programmers often include a movable wand with an antenna that is placed on the patient overlying the implanted device to facilitate reception and transmission of signals to/from the implantable device. The wand is placed over the implanted device to be proximate the device to thereby reduce the power required for transceiving and to limit RF interference with or by other nearby devices.

Programmers are particularly useful during the implantation process as the telemetric feedback from the device to the programmer can confirm integrity of the connections of leads to the implantable device after the leads are attached or, conversely, indicate faulty connections thereof. The implantable device can also telemetrically indicate its operational status to the programmer and it will be understood by one of skill in the art that correct device operation is preferably confirmed before closure of surgical incisions.

Both the programmers and PSAs previously described are typically used during an implantation procedure. The combination of these and other medical equipment as well as the number of attending personnel used in a typical implantation procedure can result in a surgery room that is relatively crowded with equipment that is often inconvenient to use due to the crowding and limited space.

From the foregoing, it will be appreciated that there is a need for medical devices offering the functionality of both current PSAs and programmers, but with increased convenience of use. It would be advantageous to provide this functionality while reducing the number of separate pieces of equipment.

SUMMARY

In one embodiment, a telemetry wand is disclosed that is connectable to a physician programmer for implantable medical devices connectable to indwelling leads, the telemetry wand comprising a telemetry coil for telemetric communication with an implantable device and connectable to a programmer, at least one terminal for connection to an indwelling lead, and electronics connected to the at least one terminal so as to be able to receive signals therefrom, evaluate the signals, and selectively control delivery of electrical stimulation pulses thereto so as to emulate an implantable device as a pacing system analyzer and wherein the telemetry wand also provides the capability to telemetrically communicate with the implantable device so as to receive data therefrom and provide programming instructions thereto.

In one embodiment, the telemetry wand further comprises a selector such that a user may select between operation of the telemetry wand for telemetric communication with an implantable device with the programmer or as the pacing system analyzer for the indwelling lead. The electronics can also include operational software operable with operating software of the programmer such that the programmer, in combination with the telemetry wand, can be selectively operated as the programmer or as the pacing system analyzer.

In one embodiment, the telemetry wand further comprises a telemetry cable and wherein connection between the telemetry wand and the programmer is via the telemetry cable and/or a display wherein the telemetry wand can display at least a subset of information received from the implantable device or commands sent thereto.

Another embodiment is a programmer and pacing system analyzer (PSA) system comprising a physician programmer having operating software, a programmer/PSA wand in communication with the programmer, and PSA application software operable with the programmer operating software such that the system provides the ability to operate both as the programmer to telemetrically communicate with an implantable device so as to extract information therefrom and deliver instructions thereto as well as a pacing system analyzer to receive signals from an indwelling lead, evaluate the signals, and selectively deliver stimulation pulses thereto.

DETAILED DESCRIPTION OF THE PREFERRED EMBODIMENT

The following description is of the best mode presently contemplated. This description is not to be taken in a limiting sense but is made merely for the purpose of describing the general principles of the illustrative embodiments. The scope of the invention should be ascertained with reference to the issued claims. In the description that follows, like numerals or reference designators will be used to refer to like parts or elements throughout.

Figure 1:
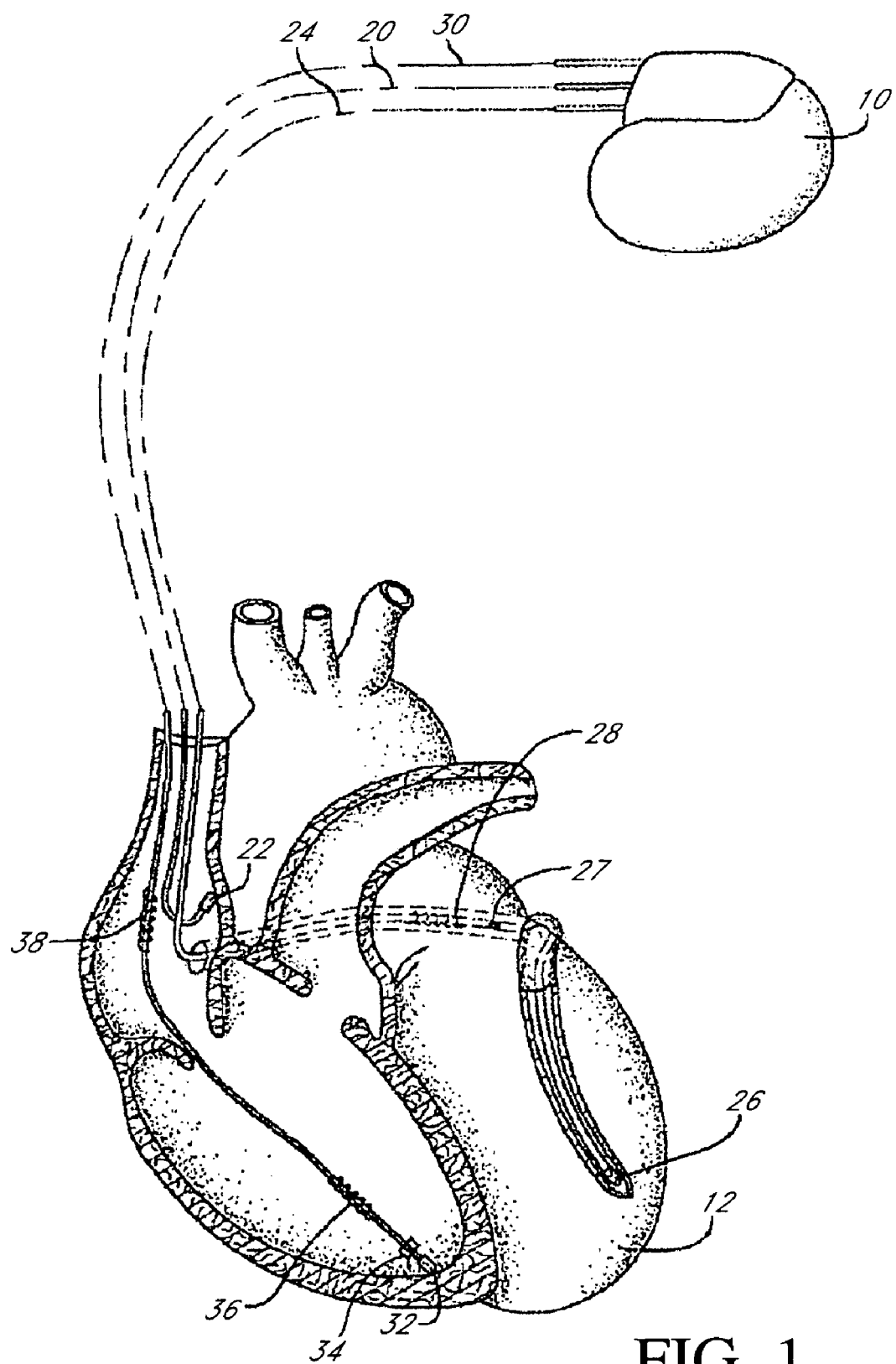
FIG. 1 is a diagram of an embodiment of an implantable cardiac device in communication with a patient's heart via three indwelling leads.

As shown in FIG. 1, there is a multi-chamber implantable stimulation device 10, referred to hereafter as "device 10" for brevity, in electrical communication with a patient's heart 12 by way of, in this embodiment, three leads, 20, 24 and 30, suitable for delivering multi-chamber stimulation and shock therapy. To sense atrial cardiac signals and to provide right atrial chamber stimulation therapy, the stimulation device 10 is coupled to an indwelling right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an indwelling right ventricular lead 30 having, in this embodiment, a right ventricular tip electrode 32, a right ventricular ring electrode 34, a right ventricular (RV) coil electrode 36, and an superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing, and shock therapy to the right ventricle.

The multi-chamber implantable stimulation device 10 is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate, or disable the appropriate circuitry in any desired combination to provide a device capable of treating the appropriate chamber(s) with cardioversion, defibrillation and pacing stimulation.

A housing for the stimulation device 10 is often referred to as the "can", "case" or "case electrode" and may be programmably selected to act as the return electrode for all "unipolar" modes. The housing may further be used as a return electrode alone or in combination with one or more of the coil electrodes, 28, 36 and 38, for shocking purposes.

Figure 2:
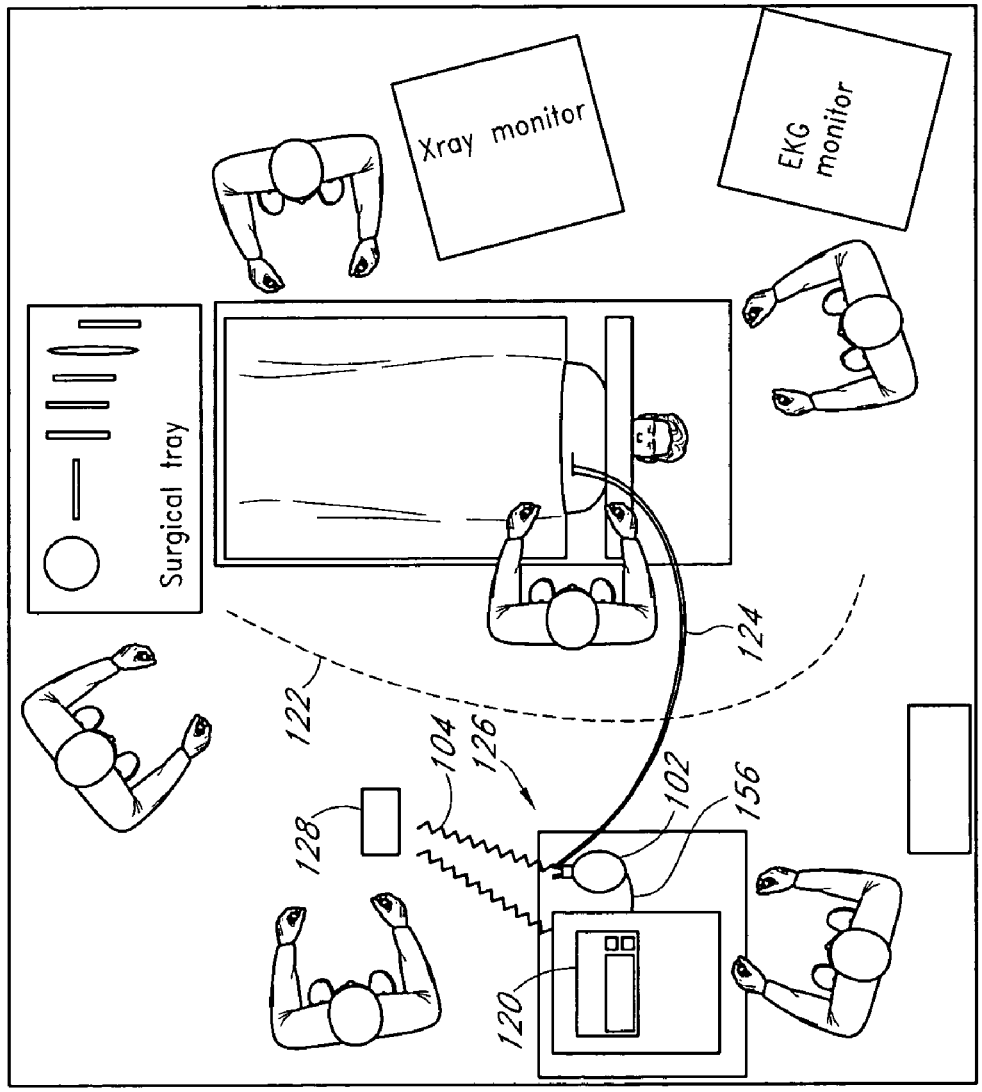
FIG. 2 shows a typical arrangement of a crowded O.R. or EP catheter lab during an implantation procedure employing embodiments of the invention.

FIG. 2 shows a typical arrangement of a crowded O.R. or EP catheter lab during an implantation procedure, including a programmer/PSA wand 102 that can communicate with a programmer 120 located outside of a sterile field 122. One embodiment includes a patient cable 124 adapted at a first end for connection to the indwelling leads 20, 24, 30, e.g. via alligator clips, and at a second end for connection to the programmer/PSA wand 102. The patient cable 124 is adapted to span the boundary of the sterile field 122 so as to allow communication thereacross and maintain the integrity of the sterile field 122. Suitable patient cables 124 are commercially available and are well known in the art.

The programmer/PSA wand 102 and programmer 120 together define a programmer/PSA system 126. The system 126 provides the ability to evaluate the connections of the leads 20, 24, 30 to the patient and their characteristics with the system. The system 126 also provides the ability to telemetrically communicate with and evaluate the performance of the device 10 with increased convenience and reduced number of support equipment devices. The system 126 provides the functionality of both PSAs and programmers but without the typical bulk and number of pieces of equipment, e.g. while eliminating the need for a separate PSA. The particular operation and advantages of the system 126 will be described in greater detail below following a more detailed description of the components of the system 126.

Figure 3:
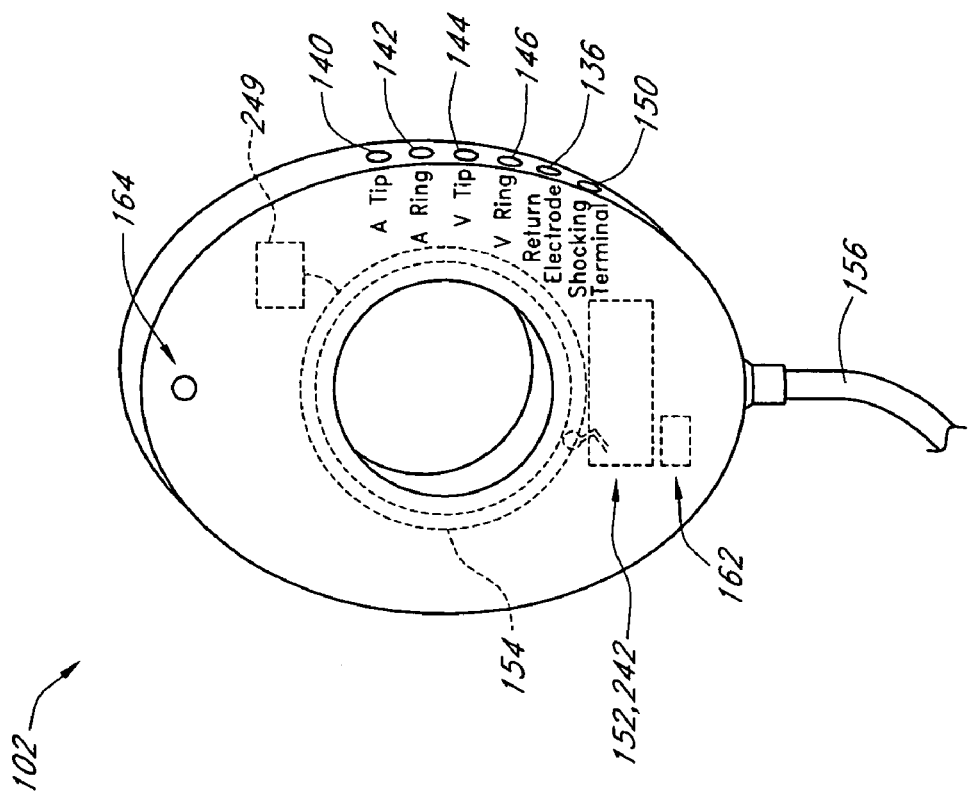
FIG. 3 is a perspective view of one embodiment of a programmer/PSA wand.

In this embodiment, the programmer/PSA wand 102 comprises a return electrode terminal 136 and a plurality of terminals 140, 142, 144, 146, and 150 for connection to the leads 20, 24, 30 as shown in FIG. 3. As the housing of the device 10 can act as a return electrode for certain operating modes of the device 10, the return electrode 136 is provided to simulate this aspect of the not necessarily present implantable device 10. The return electrode 136 can be connected to an indifferent plate positioned in the opening provided for implant or to an alligator clip, for example, that can be attached to the patient via the patient cable 124 in a variety of manners that will be well understood by one of skill in the art.

The programmer/PSA wand 102 includes, in this embodiment, an atrial tip terminal ($A_{TIP}$) 140, an atrial ring terminal ($A_{RING}$) 142, a ventricular tip terminal ($V_{TIP}$) 144 and a ventricular ring terminal ($V_{RING}$) 146. The $A_{TIP}$ terminal 140 is adapted for connection to the atrial tip electrode 22. The $A_{RING}$ terminal 142 is adapted for connection to the atrial ring electrode 27. The $V_{TIP}$ terminal 144 is adapted for connection to the left 26 or right 32 ventricular tip electrodes. The $V_{RING}$ terminal 146 is adapted for connection to the ventricular ring electrode 34. The programmer/PSA wand 102 may also include a shocking terminal 150 for connection to the left atrial coil electrode 28, the RV coil electrode 36, and/or the SVC coil electrode 38.

As mentioned, during the open portion of an implant procedure, the programmer/PSA wand 102 will typically be connected to the leads 20, 24, 30 via the patient cable 124 for evaluation while maintaining the integrity of the sterile field 122. As the physical configuration of specific examples of leads 20, 24, and 30 can vary, it will be appreciated that the corresponding configuration of the mating connections of the patient cable 124 will be adapted for ready connection to the leads 20, 24, and 30. Likewise, the exact configuration of the terminals 136, 140, 142, 144, 146, and 150 can vary to match the configuration of specific patient cables 124 and vice versa. These terminals may be embodied as one or more connectors on the wand 102. It will be generally preferred that the configuration of the terminals 136, 140, 142, 144, 146, and 150 of the programmer/PSA wand 102 will be generally closed and suitable for cleaning to remove material that may accumulate at the terminals 136, 140, 142, 144, 146, and 150. This is to facilitate maintaining the cleanliness of the programmer/PSA wand 102 as used in a clinical setting.

The programmer/PSA wand 102 also comprises electronics 152. The electronics 152 provide many of the functions of the implantable device 10 and serves to evaluate the characteristics of the leads 20, 24, 30 to confirm their proper placement and satisfactory condition prior to connection of the leads 20, 24, 30 to the device 10 and the closing of the implantation wound. The electronics 152 also allow the wand 102 to determine many of the programmed parameters that will need to be programmed into the device 10 prior to release of the patient. The composition and function of the electronics 152 will be described in greater detail below with reference to FIG. 6.

The programmer/PSA wand 102 includes a telemetry coil 154. The telemetry coil 154 is configured as a radiofrequency (RF) antenna to facilitate communication between an implantable device 10 and the system 126. The construction of the telemetry coil 154 is well understood by one of ordinary skill in the art. The composition and form of the telemetry coil 154 can vary in specific applications and is preferably configured to enable telemetric communication between the system 126 and the implantable device 10 at increased data rate and reduced power expended by the implantable device 10. The telemetry coil 154 thus facilitates communication of the device 10 with the programmer/

PSA wand 102 and with the programmer 120 so as to be able to exchange signals therewith.

Figure 4:
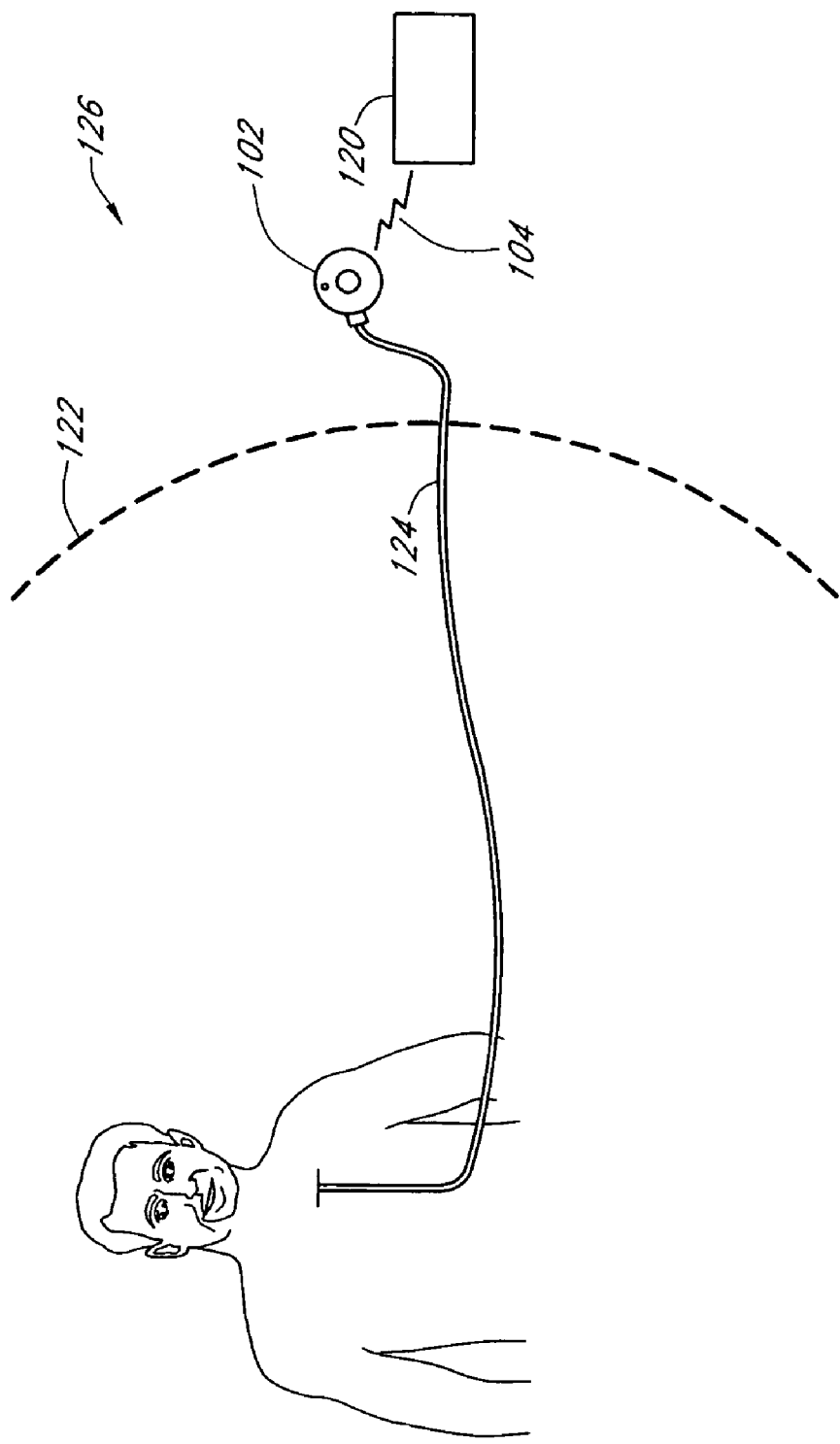
FIG. 4 is a view of a programmer/PSA wand connected to one or more indwelling leads via a patient cable during an implantation procedure.
Figure 5:
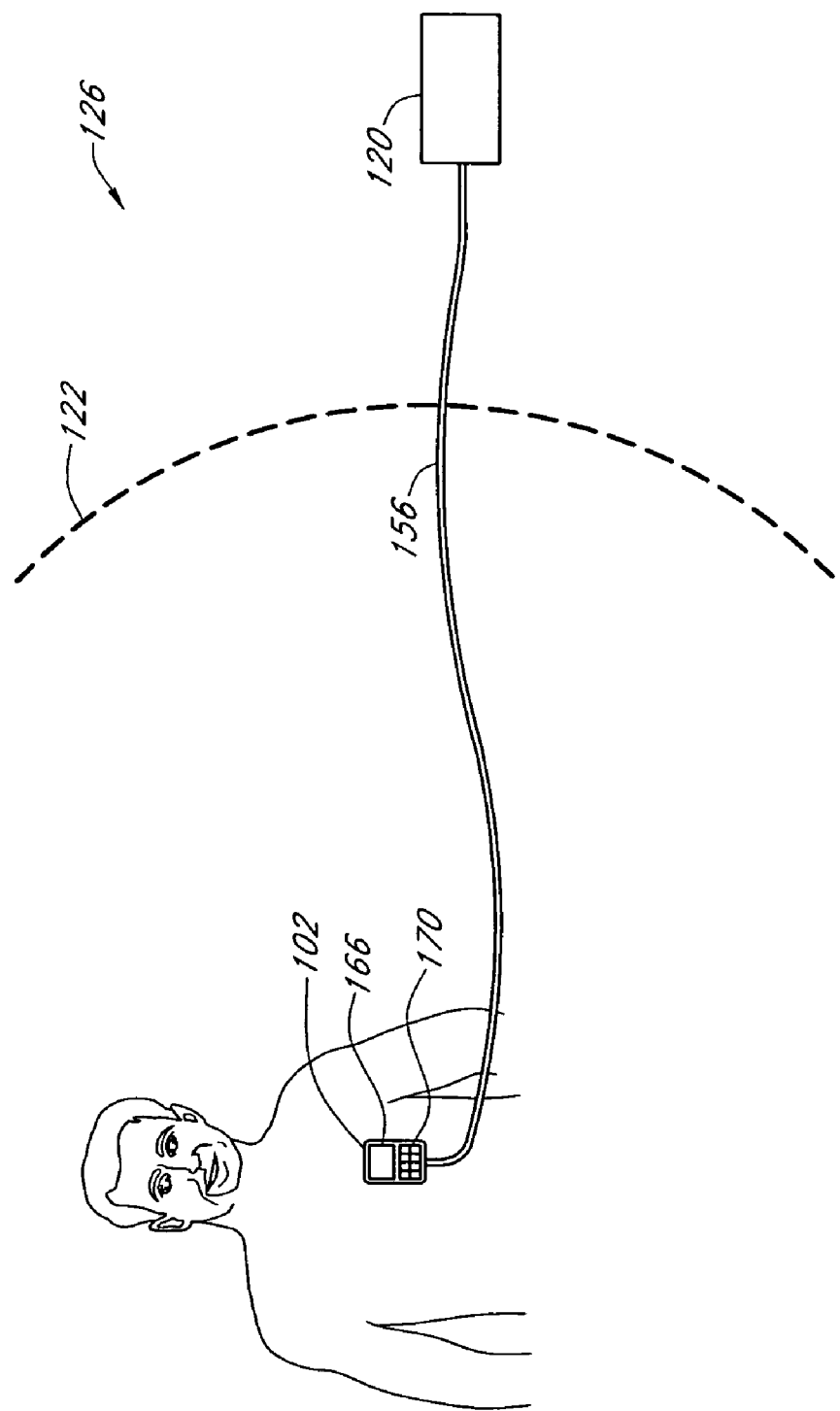
FIG. 5 is a view of a programmer/PSA wand placed adjacent a patient and in communication with a physician programmer and an implantable device.
Figure 6:
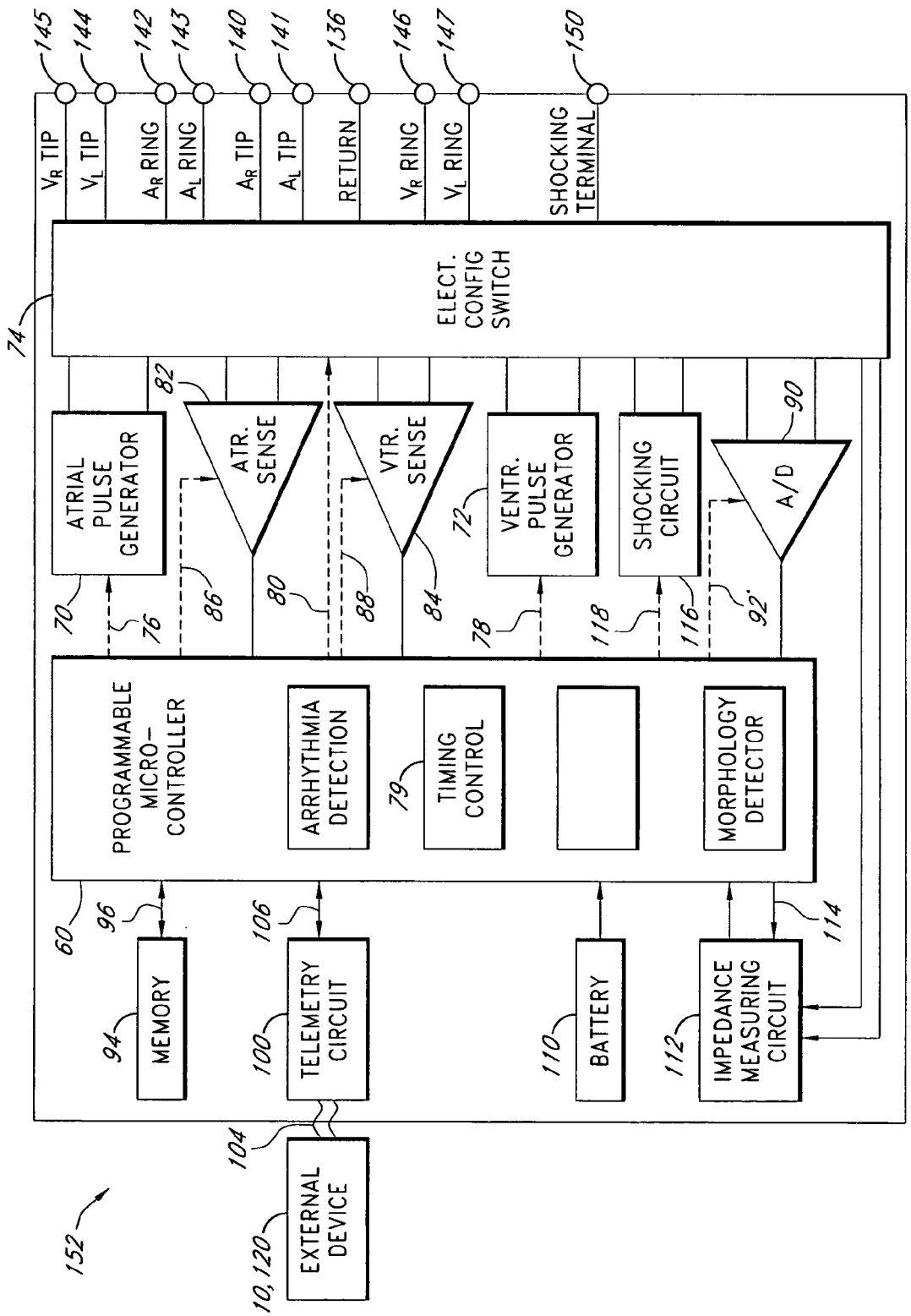
FIG. 6 is a functional block diagram of one embodiment of the electronics of a programmer/PSA system of FIG. 5 providing functionality of an implantable stimulation device.

The programmer/PSA wand 102 can, in various embodiments, be in wired communication with the programmer 120 via a telemetry cable 156 as shown in FIGS. 3 and 5 and/or via a wireless telemetry link 104 as shown in FIGS. 4 and 6. FIG. 2 shows an embodiment with both the telemetry cable 156 and a telemetry link 104. In this embodiment, the programmer/PSA wand 102 and the programmer 120 comprise infrared (IR) emitters and photodetectors with interface electronics to provide IR band transceivers. The embodiment shown in FIG. 2 also comprises one or more linking transceivers 128 configured to communicate with the programmer/PSA wand 102 and the programmer 120. The linking transceiver 128 is preferably located in an unobtrusive location, such as the ceiling of the O.R. The linking transceiver acts as an intermediary linking the programmer/PSA wand 102 and the programmer 120 and is also preferably positioned to reduce potential line-of-sight interruptions in communications. The IR telemetry link 104 of this embodiment avoids some of the difficulties of radio-frequency (RF) interference of the system 126 with or from other electronic equipment that is frequently found in a clinical setting.

In other embodiments, the telemetry link 104 comprises RF and/or other wireless communication systems, such as ultrasonic communications systems, well understood in the art and the programmer/PSA can comprise an additional transceiver 249 (FIG. 3). The telemetry link 104 can operate in a modulated manner and/or in a distinctive frequency band to reduce interference with and from other electronic equipment. Implementation of specific communication protocols for the telemetry link 104 is well understood by one of ordinary skill in the art.

In certain embodiments, the programmer/PSA wand 102 also receives electrical operating power from the programmer 120 via the telemetry cable 156. The programmer/PSA wand 102 can also receive power from a battery 110 as shown in FIG. 6 to reduce cabling in the clinical setting.

The programmer/PSA wand 102 may be employed to communicate with an implantable device 10 either during an implantation procedure or, following implantation, to reprogram, reconfigure, and/or extract information from the implantable device 10 in a manner that will be described in greater detail below. It will be understood that placement of the programmer/PSA wand 102 within the sterile field 122 e.g. during an implantation may require placement of the wand 102 in a sterile bag to maintain integrity of the sterile field 122.

The programmer/PSA wand 102 also includes a PSA/telemetry selector 162. The PSA/telemetry selector 162 allows a user to select between operation of the system 126 as a PSA or programmer. The programmer/PSA wand 102 also includes a position indicator 164. The position indicator 164 provides an indication, e.g. illumination of an LED light, to indicate proper positioning and establishment of the telemetry link 104 between the programmer/PSA wand 102 and an implantable device 10. The telemetry coil 154 is preferably configured to provide the telemetry link 104 over a location range of several centimeters with respect to the implantable device 10.

Figure 7:
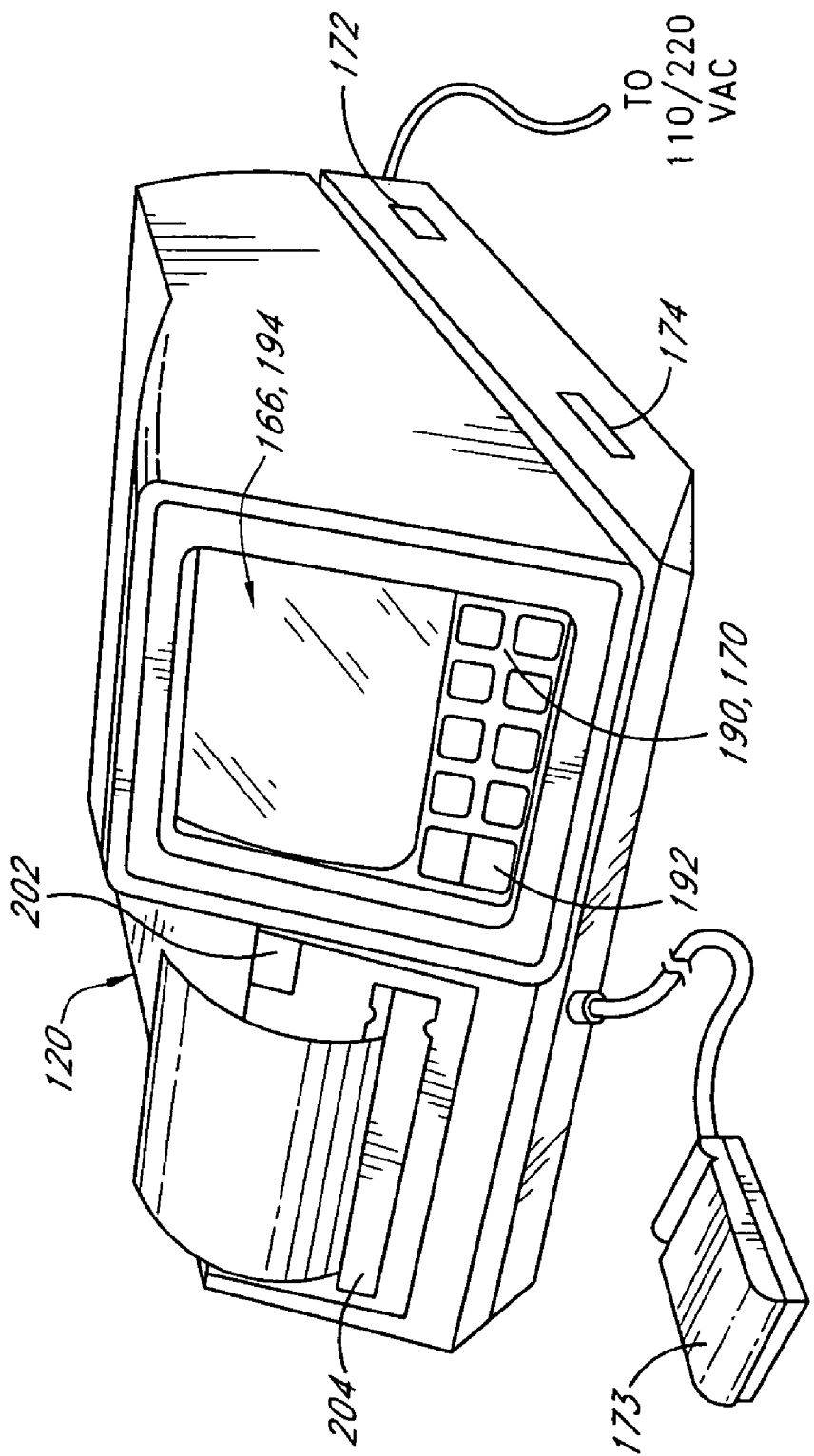
FIG. 7 is a perspective view of a programmer of a programmer/PSA system.

The system 126 also comprises at least one display 166. In certain embodiments, the display 166 is embodied within the programmer/PSA wand 102 (as shown in FIG. 5), in certain embodiments in the programmer 120 (as shown in FIG. 7), and in other embodiments at least partially in both. The display 166 presents alphanumeric and graphical information relating to lead characteristics, patient condition and responses, implantable device 10 performance and status, etc. to a user of the system 126. The display 166 can comprise a liquid-crystal display (LCD), plasma display, array of light-emitting diodes (LEDs), or other display means capable of visually presenting information to a user. In certain embodiments, the display 166 as embodied in the wand 102, can provide full display capability for the system 126 and, in other embodiments, the display 166 embodied in the wand 102 is capable of displaying a selected subset of the display capability of the system 126. Specific examples of the information that can be provided by the display 166 will be described in greater detail below with reference to the functions provided by the programmer/PSA system 126 and to FIGS. 9–13.

The programmer/PSA wand 102 also comprises at least one input device 170. Again, in certain embodiments, the input device 170 is embodied within the programmer/PSA wand 102 (as shown in FIG. 5), in certain embodiments in the programmer 120 (as shown in FIG. 7), and in other embodiments in both. The input device 170 can comprise a keyswitch matrix, keyboard, microphone and corresponding speech recognition software, and/or can be embodied as a touchscreen aspect of the display 166. The input device 170 enables a user to input information and to select among various operational controls of the programmer/PSA wand 102 and system 126.

In certain embodiments, the input device 170 comprises programmable and/or special function keys providing predefined functions of the system 126. Specific examples of functions and inputs available to a user via the input device 170 of the programmer/PSA wand 102 will be described in greater detail below with reference to functions provided by the programmer/PSA system 126 and to FIGS. 9–13.

FIG. 6 is a functional block diagram of the pacing and sensing electronics 152. The electronics 152 function similarly to the implantable device 10 during an implantation procedure. It will be understood that the electronics 152 as described herein includes comparable functionality to a true device 10, however in specific applications all of the components of the electronics 152 described herein need not be included or may be embodied elsewhere. At the core of the electronics 152 is a programmable microcontroller (CPU) 60 which controls the various modes of operation for evaluation of the leads 20, 24, 30. The microcontroller 60 includes a microprocessor, or equivalent control circuitry, for sensing and controlling the delivery of stimulation pulses and may further include RAM and/or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 6, an atrial pulse generator 70 generates pacing stimulation pulses for delivery by the atrial right tip terminal 140, atrial left tip terminal 141, atrial right ring terminal 142, atrial left ring terminal 143, and the return (case) 136. A ventricular pulse generator 72 generates pacing stimulation pulses for delivery by the ventricular left tip terminal 144, ventricular right tip terminal 145, ventricular right ring terminal 146, ventricular left ring terminal 147 and the return (case) 136. It is understood that in order to provide stimulation in each of the four chambers of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses. It will also be understood that in particular embodiments, a subset of the terminals 136, 140, 141, 142, 143, 144, 145, 146, 147, and 150 are provided.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, post-ventricular atrial refractory period (PVARP) intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart 12. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may evaluate the sensing polarity independent of the stimulation polarity.

Each sensing circuit, 82 and 84, preferably employs one or more low power amplifiers with programmable gain and/or automatic gain control, bandpass filtering, and a threshold detection circuit, as known in the art, to selectively sense the cardiac signal of interest.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart 12. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

The electronics 152 utilizes the atrial and ventricular sensing circuits, 82 and 84, to sense cardiac signals. As used herein "sensing" is reserved for the noting of an electrical signal, and "detection" is the processing of these sensed signals and noting the presence of an event.

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or transmission by the programmer/PSA wand 102 to the programmer 120. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60, or other detection circuitry, for detecting an evoked response from the heart 12 in response to an applied stimulus, thereby aiding in the detection of "capture". Capture occurs when an electrical stimulus applied to the heart 12 is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via a control signal 92 to sample the cardiac signal that falls in the capture detection window and, based on the waveform, determines if capture has occurred.

Capture detection may occur on a beat-by-beat basis or on a sampled basis. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, for subsequent programming of the device 10 in order to customize the operation of the device 10 to suit the needs of a particular patient. Such operating parameters define, for example, pacing pulse amplitude, pulse duration, electrode polarity, rate, sensitivity, and automatic features.

As previously described, the memory 94 can also store sensed data relating to cardiac activity. A feature is the ability to sense and store a relatively large amount of data (e.g., from the data acquisition system 90), which data may then be used for subsequent analysis to guide the programming of the device 10. Advantageously, the operating parameters of the implantable device 10 may be non-invasively programmed through a telemetry coil 154 in telemetric communication with the device 10 and the programmer 120.

As previously mentioned, the programmer/PSA wand 102 may include a battery 110 which provides operating power to the circuits shown in FIG. 6. Alternatively, as previously described, the wand 102 may receive electrical power from the programmer 120 via the telemetry cable 156.

As further shown in FIG. 6, the electronics 152 is shown as having an impedance measuring circuit 112 which is enabled by the microcontroller 60 via a control signal 114. The known uses for an impedance measuring circuit 112 include, but are not limited to, lead impedance evaluation of proper lead positioning or dislodgment. The impedance measuring circuit 112 is advantageously coupled to the switch 74 so that any desired electrode 20, 24, 30 may be evaluated.

The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38 via the shocking terminal 150. As noted above, the return electrode 136 may act as an active electrode in combination with the RV coil electrode 36, or as part of a split electrical vector using the SVC coil electrode 38 or the left atrial coil electrode 28 (i.e., using the RV coil electrode 36 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

FIG. 7 is a perspective view of one embodiment of the programmer 120 of the system 126. The programmer 120 is a stationary portion of the programmer/PSA system 126 and includes typically bulkier items and/or items that are more power consumptive than those of the aspects of the programmer system 126 embodied in the programmer/PSA wand 102. The programmer 120 also comprises portions of the programmer system 126 that do not need to be in close proximity to patients in order to permit proper operation of the system 126 as provided with the programmer/PSA wand 102. In certain embodiments, the programmer 120 is provided with line electrical service for electrical power and thus has practically an unlimited amount of electrical power available. In other embodiments, the programmer 120 is provided with a portable electrical power source, such as batteries, (not shown) to enable the system 126 to be more readily portable. As previously mentioned, in certain embodiments, the programmer/PSA wand 102 receives operational electrical power from the programmer 120 via the telemetry cable 156 and thus, in these certain embodiments, the programmer/PSA wand 102 receives electrical power from a line source or a portable source in accordance with the programmer 120.

The programmer 120 comprises a wand connector 172 for connection to the programmer/PSA wand 102 in those embodiments including a telemetry cable 156. The wand connector 172 is adapted to physically and electrically mate with the telemetry cable 156 so as to allow the telemetry cable 156 and thus the programmer/PSA wand 102 to be removably connected to the programmer 120.

The programmer 120 also comprises removable storage 174. The removable storage 174 provides the capability of storing data on a removable media in a non-volatile manner. The removable storage 174 in the embodiment shown in FIG. 7 comprises a removable disk, however, in other embodiments the removable storage 174 can alternatively or in addition comprise a non-volatile solid state storage system, such as a flash memory system or an optical storage system, such as a writeable optical disc.

Figure 8:
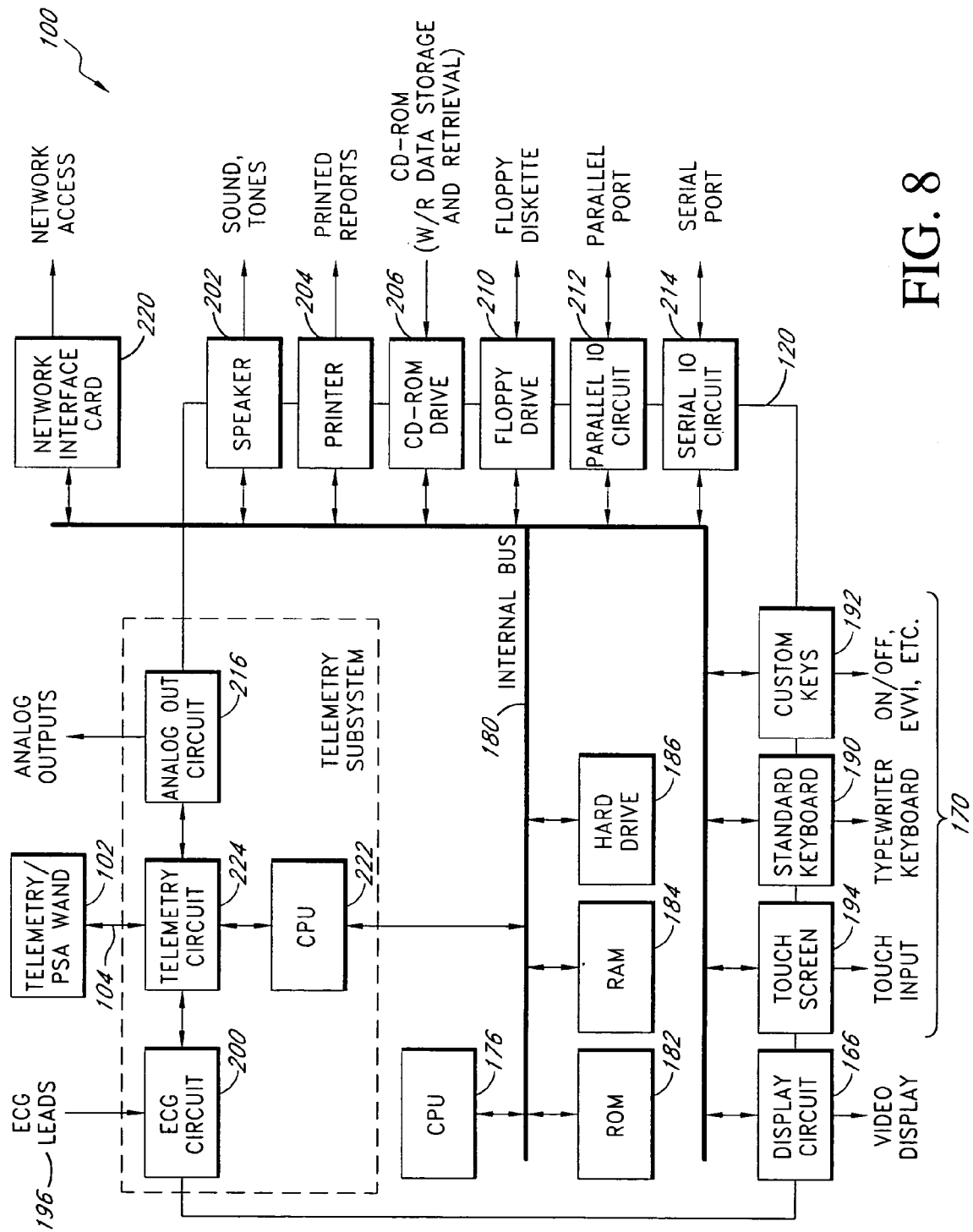
FIG. 8 is a functional block diagram of the programmer of FIG. 7.

FIG. 8 is a functional block diagram of one embodiment of the programmer 120 illustrating greater details thereof. A CPU 176 is in communication with an internal bus 180. The internal bus 180 provides a common communication link and power supply between the various electrical devices of the programmer 120, including the CPU 176. The programmer 120 also comprises ROM 182, RAM 184, and a hard drive 186 in communication with the internal bus 180. The ROM 182, RAM 184, and hard drive 186 provide temporary memory and non-volatile storage of data in a well known manner. In particular, the ROM 182, RAM 184, and hard drive 186 can store programmed control programs and commands for upload to an implantable device as well as control programs for display of data received from an implantable device as is well understood in the art. It will be appreciated that, in certain embodiments, alternative data storage/memory devices, such as flash memory, can be included or replace at least one of the ROM 182 and hard drive 186.

In certain embodiments, the programmer 120 also comprises input devices 170 comprising, in this embodiment, a keyboard 190, a plurality of custom keys 192, and a touchscreen 194 aspect of the display 166. The keyboard 190 facilitates entry of alphanumeric data into the programmer system 126. The custom keys 192 are programmable in order to provide one touch functionality of predefined functions and/or operations of the system 126. The custom keys 192 may be embodied as dedicated touch keys and/or as predefined areas of the touchscreen 194. The custom keys 192 can provide overlapping, i.e., identical functions to those provided by the input device 179 as embodied in the programmer/PSA wand 102, however, the custom keys 192 can also provide additional functions than the input device 170 of the programmer/PSA wand 102. The input devices 170 can also comprise a graphical-user-interface provided via the touchscreen 194 aspect of the display 166 and/or via a mouse 173.

In certain embodiments, the programmer 120 also comprises a speaker 202 and a printer 204 in communication with the internal bus 180. The speaker 202 is adapted to provide audible alerts and signals to a user and the printer 204 is adapted to provide a printed read-out of information as generated or monitored by the system 126.

The programmer 120 can also comprise a CD drive 206 and a floppy drive 210 which together comprise the removable storage 134. The CD drive 206 and the floppy drive 210 provide removable data storage and read capability for the programmer system 126 in a well understood manner.

In this embodiment, the programmer 120 also provides interfaces including a parallel input-output (IO) circuit 212, a serial IO circuit 214, an analog output circuit 216, and network interface card 220. These interfaces 212, 214, 216, 220 provide a variety of communication capability with other devices and/or networks in a manner well understood in the art.

In this embodiment, the programmer 120 further includes a telemetry CPU 222 and telemetry circuit 224 that facilitate the establishment and maintenance of the telemetry link 104. The telemetry circuit 224 is adapted to allow the programmer 120 to establish at least one wired or wireless telemetry link 104 (FIG. 4) with the programmer/PSA wand 102. The programmer/PSA wand 102 can then have wired or wireless communication with the PSA electronics 152. The wand coil 154 can interface with the telemetry circuit 224 or there can be wireless communication between the telemetry circuit 224 and the additional transceiver 249 (FIG. 3) so as to form the telemetry link 104.

Figure 9:
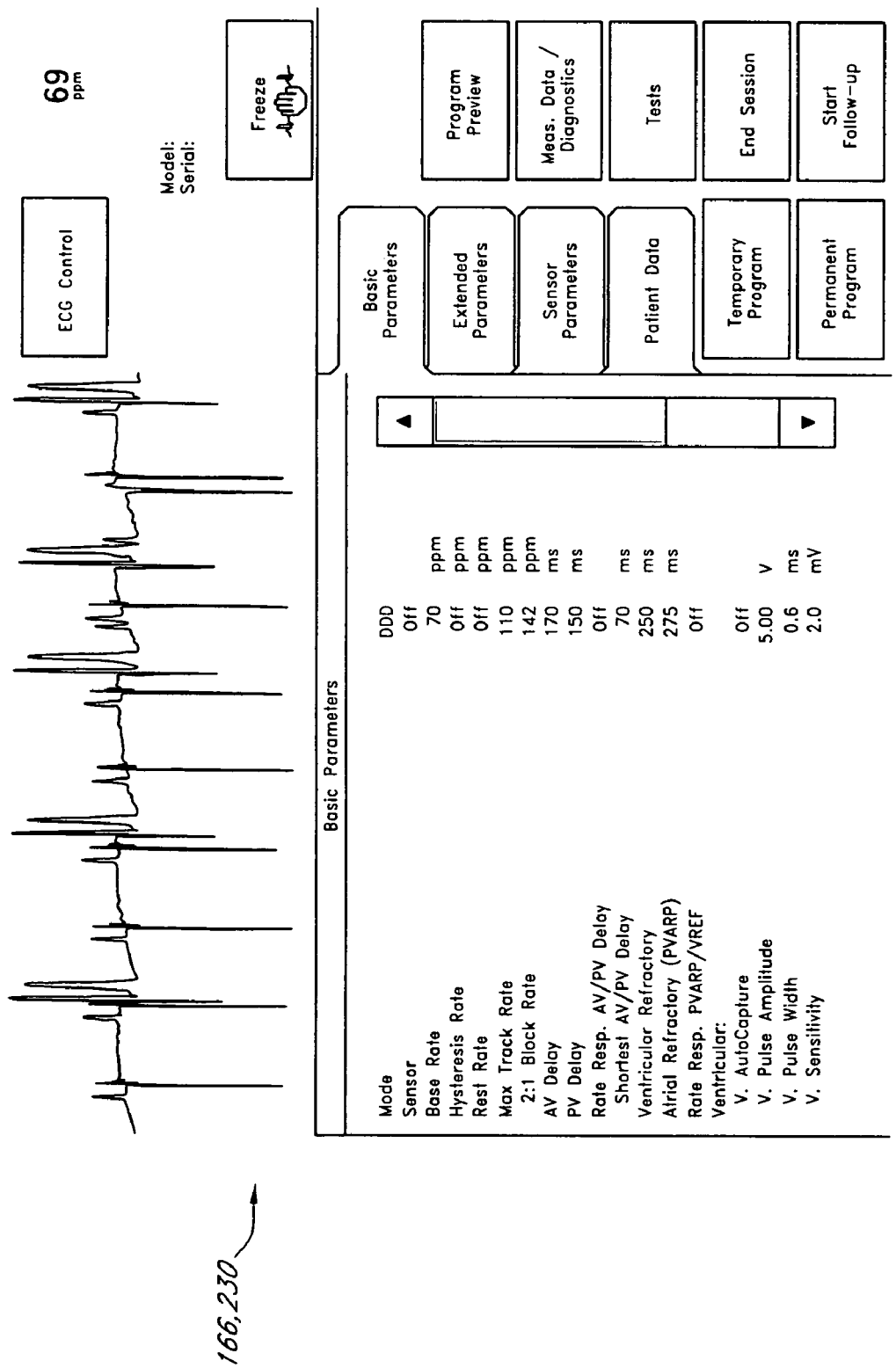
FIG. 9 is an example of a display screen showing the programmer functionality of the programmer/PSA system of FIG. 3.

In various embodiments of the system 126, functions provided by at least one of the input devices 170 of the programmer 120 and/or the programmer/PSA wand 102 include selection of an electrocardiogram (ECG) and/or an intracardiac electrogram (IEGM) for display on the display 166 for simultaneous or separate display. An ECG signal is displayed in accordance with surface signals received from the patient via a plurality of ECG leads 196 in a manner well understood by one of ordinary skill in the art. In the embodiment illustrated in FIG. 8, the ECG leads 196 provide signals to an ECG circuit 200 of the system 126. In various embodiments, the system 126 then displays the ECG waveform in a variety of known formats, such as a Lead I, Lead II, or Lead III configuration on at least one of the display(s) 166 such as is shown in FIG. 9. The input devices 170 also provide the capability for a user to select among the various lead configurations available. The display 166 can also simultaneously display ECG and IEGM waveforms.

Another function that is provided, in certain embodiments, by at least one of the input devices 170 includes access to an automatic physician follow-up diagnostic to verify/monitor device operation, patient condition, records of past anomalous cardiac events, records of therapy provided, implantable device battery charge state, etc. In certain embodiments, the system 126 can also provide emergency ventricular inhibited pacing (VVI) and/or fibrillation shock activation via at least one of the input devices 170. The system 126 can also provide a feedback indication of placement of the programmer/PSA wand 102 with respect to an implantable device via a signal strength indication on at least one of the display(s) 166 and/or via the amplitude or tone of an audible indicator as well as the indicator 164. The input devices 170 can also provide up-down scrolling through available functions or operations as well as selection of available functions.

FIG. 9 illustrates one embodiment of functions and information that can be displayed on the display(s) 166 in a programmer mode 230. However, it is to be understood that a variety of additional functions and data can be provided and made available via the input devices 170 and the display(s) 166 in various embodiments of the system 126. It should also be understood that the functions and data made immediately available via the display(s) 166 and the input devices 170 can be programmable and that the functions and data used in a specific application may be a subset of a broader set available via the system 126.

The display 166 in the embodiment shown in FIG. 9 presents a surface ECG waveform and a plurality of user selectable status fields including base rate, ventricular refractory, etc. The display 166 also presents functions that may be selected or deselected via the system 126, such as ventricular autocapture, which, in this embodiment, is deselected. The system 126 also provides the capability to telemetrically set operating parameters of the implantable device 10, such as the base rate, which in this example is currently set at 70 paced beats per minute (ppm). The display 166 provides the ability to scroll through a window to view additional information and/or available functions. The display 166 of this embodiment also provides custom keys 192 that provide selection among, for example, display of sensor parameters, patient data, etc. It should be appreciated that, in certain embodiments, the display 166 can comprise aspects of the input devices 170 such as the touch screen 194. Certain aspects of the input devices 170 can also comprise aspects of the display 166 such as the custom keys 192 that include a data input function and also a data display function.

Figure 10:
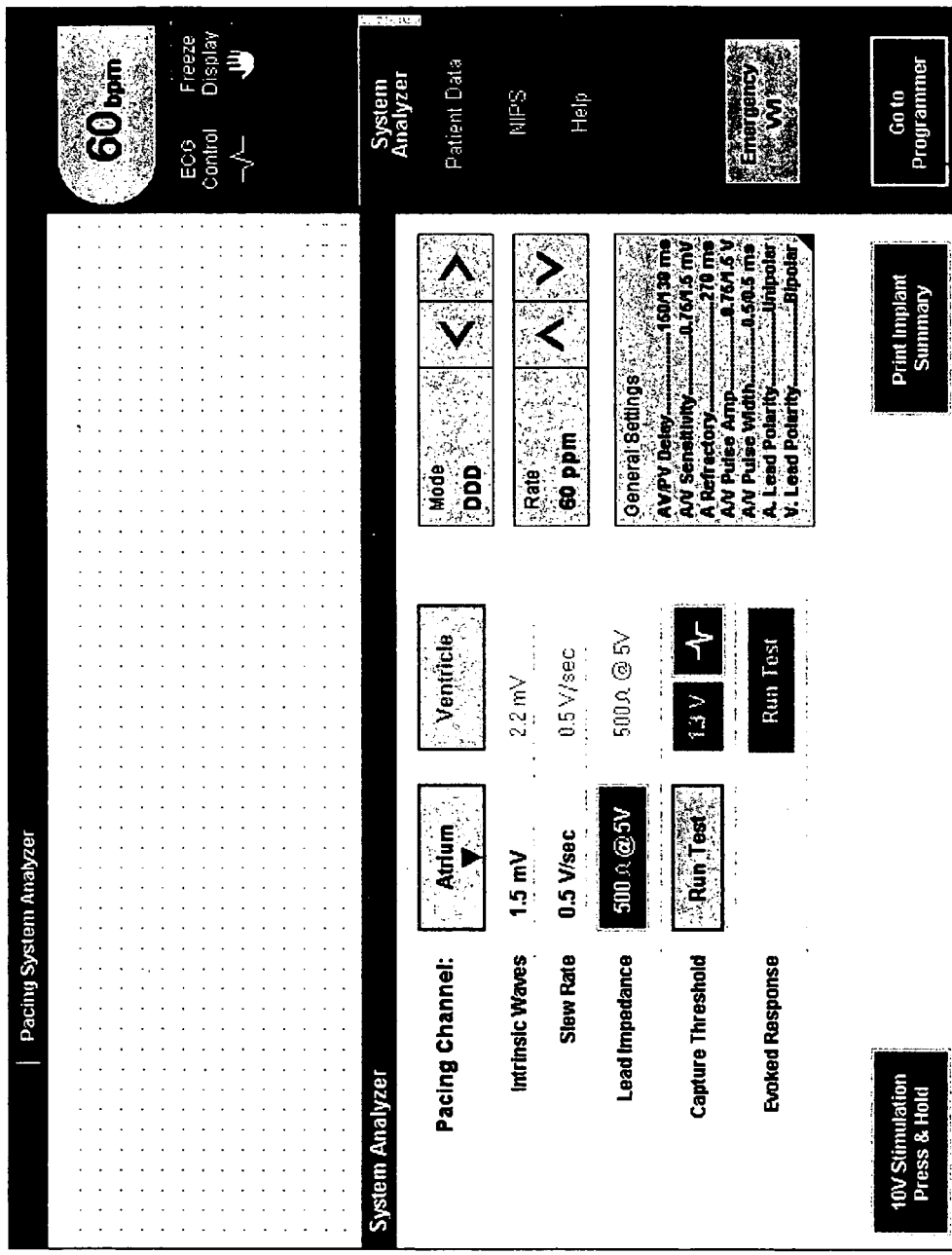
FIG. 10 is an example screen shot of a PSA lead verification screen.

FIG. 10 illustrates one embodiment of a screen shot of the display 166 of the system 126 in a PSA mode 240. As previously mentioned, selection among the programmer mode 230 and the PSA mode 240 is made via operation of the selector 162 as well as other manners. The embodiment of the PSA mode illustrated in FIG. 10 shows the main user interface for the system 126, lead verification, which provides the majority of the PSA clinical functionality. This aspect of the PSA mode 240 allows for rapid review of intrinsic beats and lead impedances and performance of threshold testing while also providing flexible IEGM and ECG capabilities and pacing functions. Functions provided also include administrative tasks, such as for example, entering patient information, lead type and device serial numbers and printing an implant summary report. In certain embodiments, user help information may also be provided via the PSA mode 240.

In the illustrative embodiment depicted in FIG. 10, information is shown from a previous ventricular lead test which results are still shown on the display 166. In particular, the ventricular lead tests return values of intrinsic waves, in this example of 2.2 millivolts, a slew rate of 0.5 volts per second, and a lead impedance of 500 ohms at 5 volts. FIG. 10 also illustrates current atrial lead testing indicating, in this example, intrinsic waves at 1.5 millivolts, a slew rate of 0.5 volts per second and a lead impedance of 500 ohms at 5 volts. The display 166 also provides additional information in this embodiment such as that the mode is DDD at a rate of 60 ppm, AV/PV delay of 150/130 milliseconds, a unipolar atrial lead polarity and a bipolar ventricular lead polarity. The display 166 also provides user input 170 which, in this example, includes an emergency VVI, a control for printing an implant summary, and the selector 162, which, in this embodiment is denoted with the notation "go to programmer." The display 166 also provides the capability to select other aspects of the PSA mode 240, such as, for example in this illustration, selection of a 10 volt stimulation.

Figure 11:
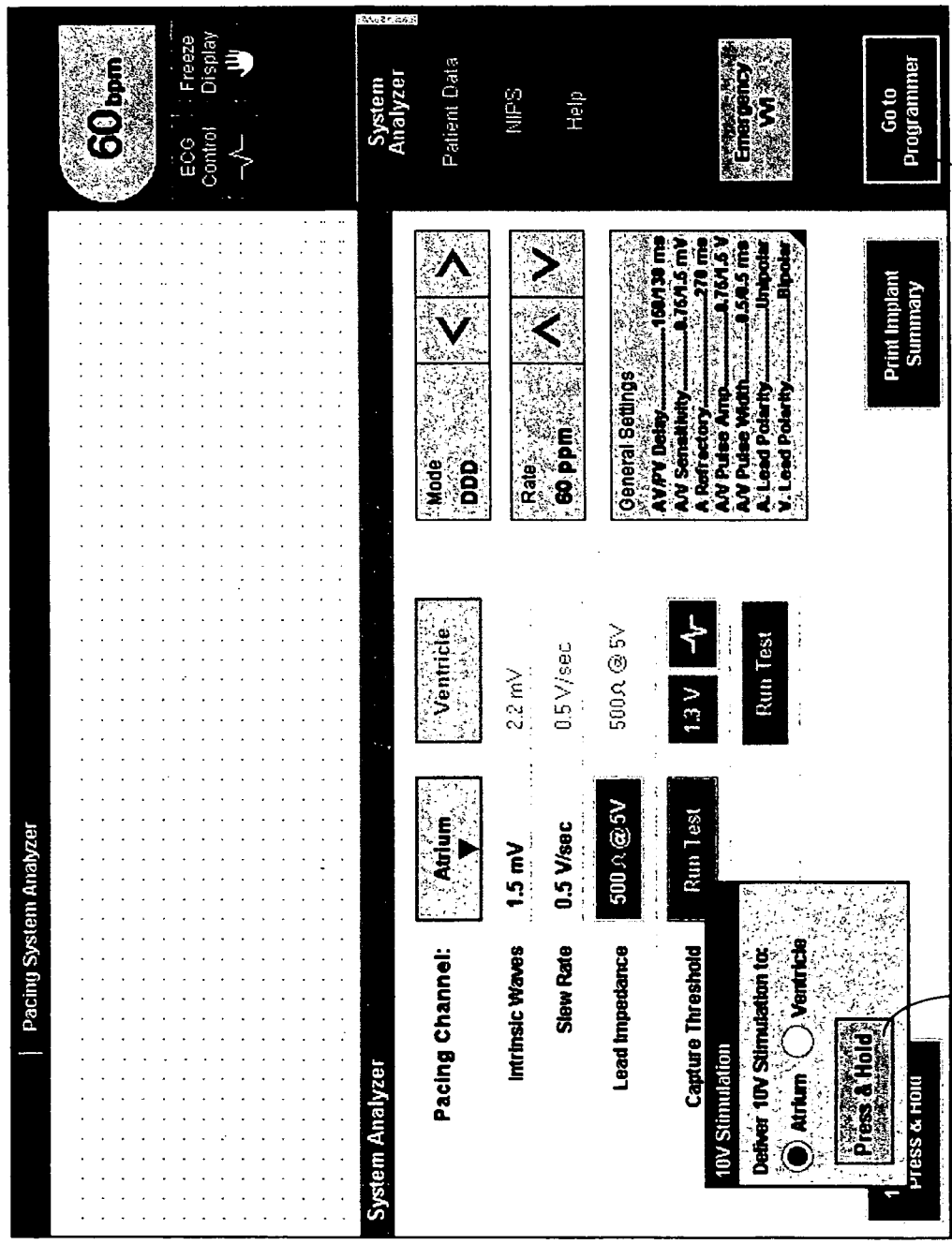
FIG. 11 is an example screen shot of a PSA 10V chest wall stimulation test screen.

FIG. 11 illustrates operation of the system 126 during a 10 volt stimulation and as shown in FIG. 11 allows for selection between the atrium and the ventricle and an activation control denoted in this embodiment as the user input 170 identified as "press and hold."

Figure 12:
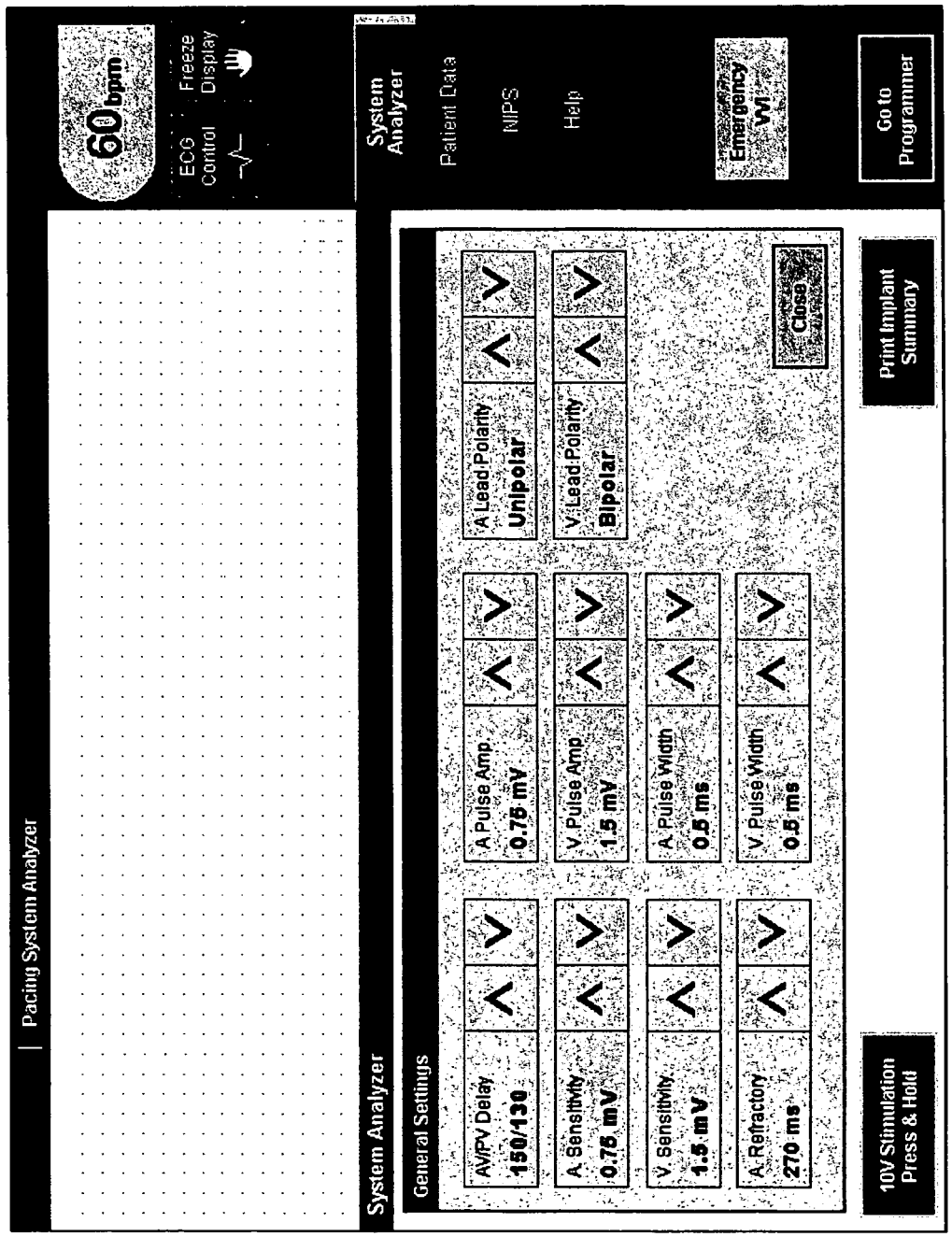
FIG. 12 is an example screen shot of a PSA general settings screen.

FIG. 12 illustrates an aspect of the PSA mode 240 comprising an illustration of general settings, modes and rates. The aspects of the PSA mode 240 illustrated in FIG. 12 indicate information provided with selection of a "general setting" control. In this aspect, new settings can be established among the various parameters. In this embodiment, this would be achieved by pressing an area of each parameter control where indicated by its label and present value which can bring up a sub-window showing possible parameter options. Alternatively using the indicated up and down arrows, a user may move the parameter through the available options sequentially. Among the parameters available for settings can include atrial sensitivity, which in this embodiment is current set at 0.75 millivolts, an atrial pulse width which is currently set at 0.5 milliseconds, and an atrial lead polarity which is currently unipolar.

Figure 13:
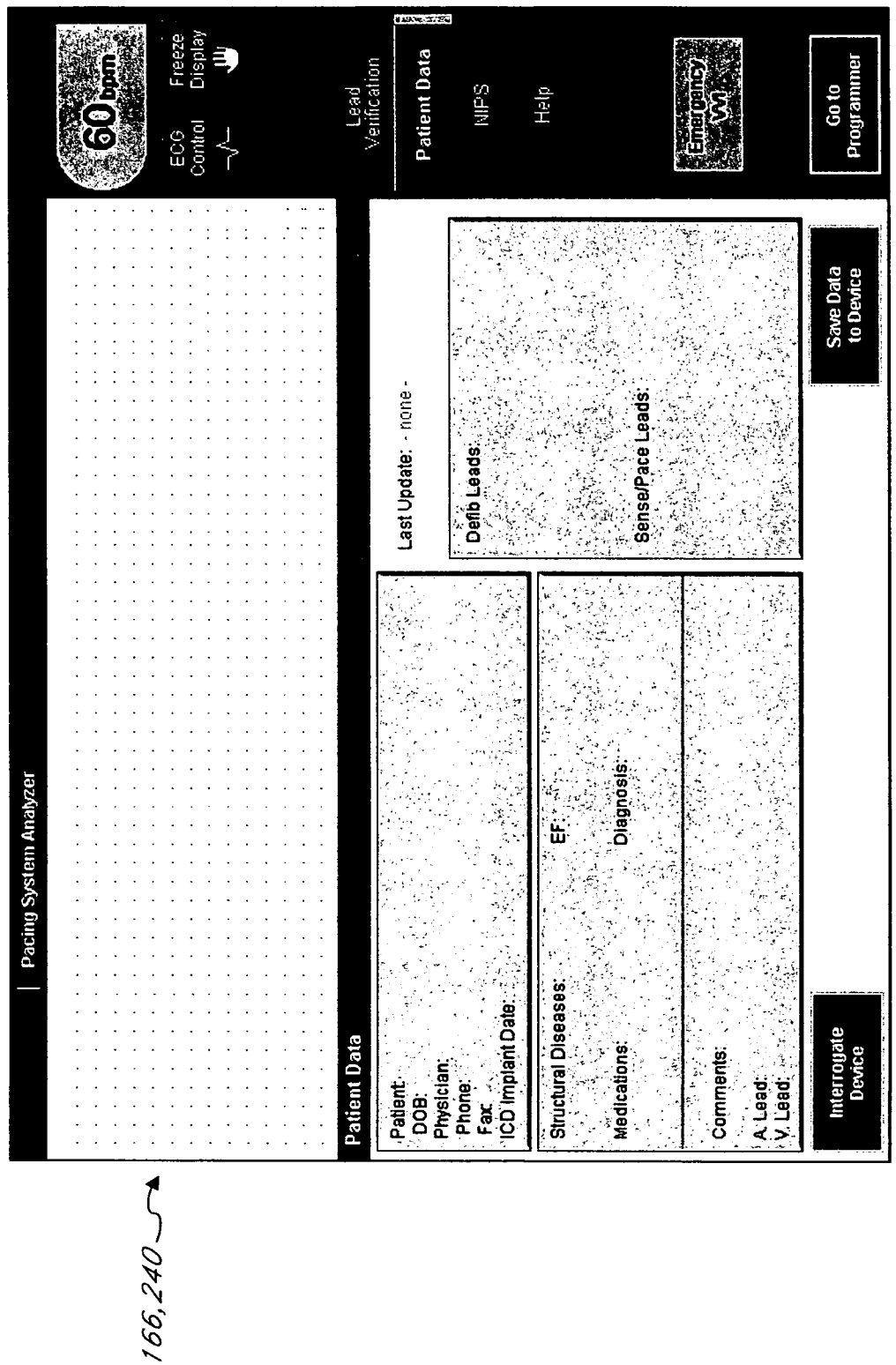
FIG. 13 is an example screen shot of a PSA mode patient data screen.

FIG. 13 illustrates aspects of the PSA mode 240 where patient data may be entered. In particular, in this example, fields are provided for the patient name, date of birth, physician, any structural diseases or medications, the implant date for, in this example, the ICD, and comments relating to the atrial and ventricular leads. A field is also provided for the last update which, in the illustrated example, has no present values. It can be seen that in this example user inputs 170 are also provided to interrogate the device and save data to the device.

The system 126 also includes PSA application software 242 which is adapted for execution on the microcontroller 60. In certain embodiments, the PSA application software 242 and programmer/PSA wand 102 are adapted to provide the improved functionality described herein when connected and installed on known programmers. This aspect provides the opportunity to provide the advantages of the system 126 described herein to existent programmers with minimal expense. In particular, the PSA application software 242 may be installed in the programmer/PSA wand 102 connected to a programmer in lieu of conventional telemetry wands thus providing increased functionality to existing clinical equipment. The PSA application software 242 would typically be installed to operate with the programmer 120 hardware which would include the CPU 176, RAM 184, etc. The PSA application software 242 is designed such that switching back and forth between the programmer mode 230 and PSA mode 240 can be readily effected from within an active session of the programmer 230 or PSA 240 modes, respectively. Also, the current system state is maintained in the programmer 230 and PSA modes when the other mode is selected.

One advantage of the system 126 is the capability in the PSA mode 240 to accept and input patient data. In particular, the PSA mode 240 allows attending clinical personnel to input patient data that has previously typically been done with a programmer. By providing the functionality of allowing patient data input in the PSA mode 240, the system 126 enables the attending clinical personnel to perform this operation without switching back and forth between the PSA mode 240 and the programmer mode 230 or between separate programmer and PSA equipment, thereby providing a more efficient procedure with fewer possible software or hardware related complications and/or delays.

Figure 14:
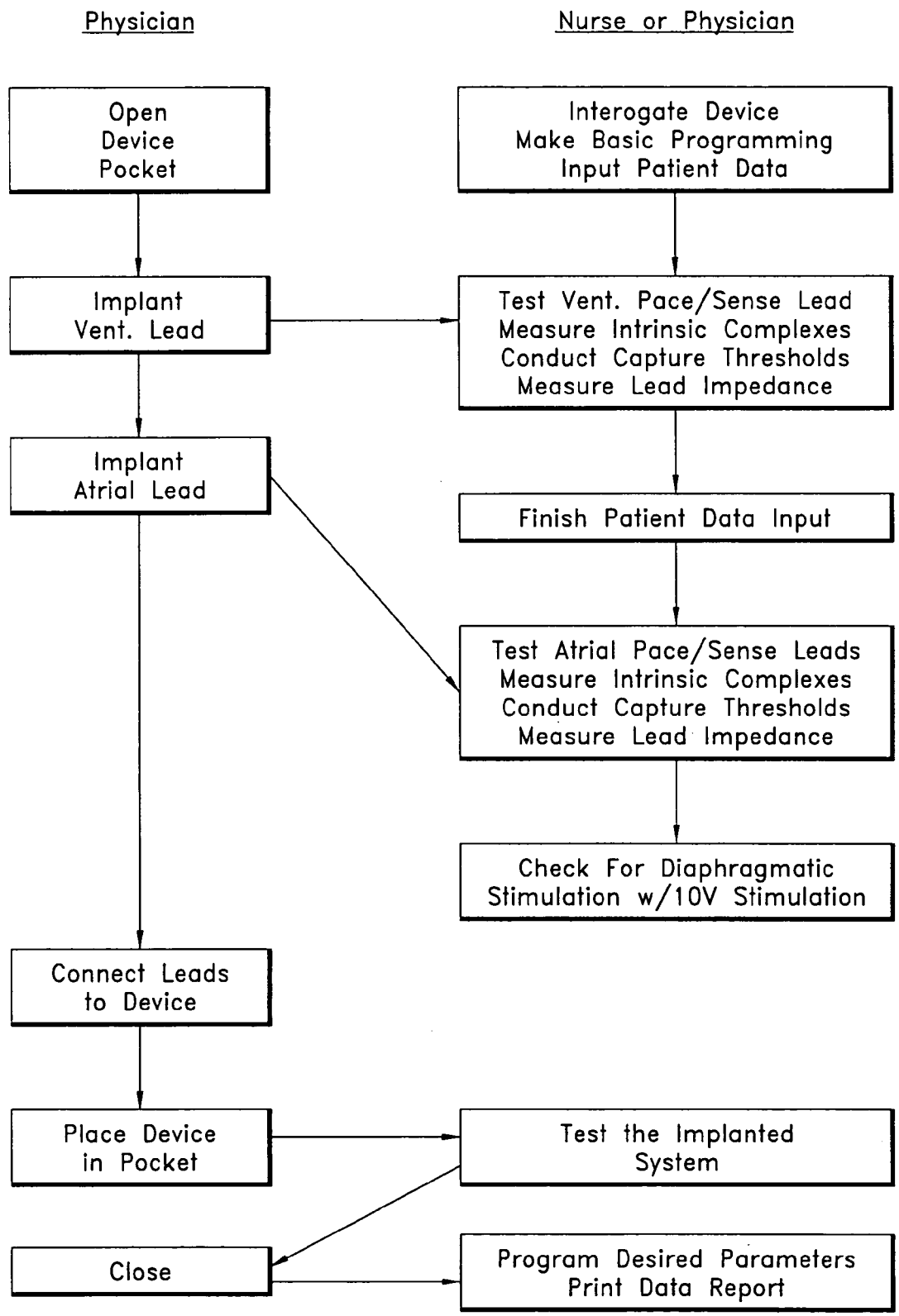
FIG. 14 is a flow chart showing an overview of the use of the programmer/PSA system during an implantation procedure.

FIG. 14 is a flowchart showing an overview of one embodiment of use of the system 126 during a typical implantation procedure. For this embodiment, the flowchart is divided between actions which would be performed, typically, by a physician and those performed by non-physician personnel, such as a nurse. In other embodiments, the physician performs both sets of tasks, thus the actions referred to below as performed by the nurse can be performed by a physician as well. The physician typically performs the invasive procedures of the implant and the nurse performs the measurements and programming of the device 10 and the leads 20, 24, 30 with use of this system 126.

The physician would begin the implantation procedure by opening the patient's chest surgically and preparing a pocket to receive the device 10. While the physician is performing this procedure, the nurse would interrogate the new device 10, begin basic programming of the device 10, and begin inputting patient data which, as described, can be performed under the PSA mode 240 of the system 126. The physician would then implant the ventricular lead and following the implant the nurse would test the ventricular pace/sense lead, measure intrinsic complexes, conduct capture threshold tests, and measure the lead impedance, again with use of the PSA mode 240 of the system 126.

It is to be noted that the operation performed while the physician is preparing a pocket to receive the device in the prior art is performed by the nurse using a programmer. The actions performed following implantation of the ventricular leads by the nurse would be performed with the use of a PSA in the prior art. Thus it will be appreciated that, in the prior art, the nurse must switch between separate pieces of clinical equipment, whereas with the illustrative embodiments disclosed herein, the nurse may continue using the same piece of equipment and in the same operating mode.

The physician would then implant the atrial lead and concurrently the nurse would finish inputting the patient data, again with use of the PSA mode 240 of the system 126. In the prior art, the nurse would typically need to, again, switch back to the programmer to finish entering the patient data. Following implantation of the atrial lead by the physician and the entering of the patient data by the nurse, the nurse would then test the atrial pace/sense leads, measure intrinsic complexes, conduct capture thresholds, and measure the lead impedance again with the PSA mode 240 of the system 126. Similarly, in the prior art, a nurse would need to switch back to a PSA to conduct these measurements. Once these measurements are complete, the nurse would then check for diaphragmatic stimulation with a 10 volt stimulation again, with use of the PSA mode 240 of the system 126.

Then, the physician would connect the leads to the device 10 and place the device 10 in the prepared pocket. The nurse then tests the implanted systems which, in the prior art would require switching back to a programmer, however, with the system 126 may still be performed with the same pieces of equipment in the same operating mode. Assuming a successful result of the tested implanted system, the physician would then close the patient and the nurse would program desired parameter settings and print out a measured data report for the chart and/or the doctor's records. This final step of the implantation as performed by the nurse would be performed with the use of a programmer in the prior art or with the system 126.

It will be appreciated by one of skill in the art that while the steps of the implantation of the device 10 by the physician are the same as in the prior art and the measurement and programming performed by the nurse are similar, in the prior art, the nurse starts with a programmer, switches to a PSA, switches back to a programmer, switches back to the PSA, and finishes with a programmer. Thus, the prior art typically indicates four switches back and forth among the separate pieces of equipment. With the system 126, as described herein, the nurse can perform all these tasks without switching back and forth between separate pieces of clinical equipment or switching back and forth between operating modes of the system 126. This aspect provides increased efficiency for the clinical personnel in the implantation procedure, reduces need for clinical equipment and introduces fewer possibilities for error and/or malfunction by avoiding switching back and forth between separate pieces of equipment or operating modes.

Although the illustrative embodiments have been shown and described, it will be understood that various omissions, substitutions and changes in the form of the detail of the device illustrated may be made by those skilled in the art. Consequently, the scope of the invention should not be limited to the foregoing description but is to be defined by the appended claims.

What is claimed is:

1. A system comprising:
   a physician programmer including operating software for programming an implantable medical device including pacing/sensing electronics and one or more indwelling leads, and
   a telemetry wand comprising:
   a housing;
   telemetry circuitry within the housing and operative to wirelessly communicate with pacing/sensing electronics in the implantable medical device;
   communication circuitry within the housing and operative to communicate with the physician programmer;
   at least one terminal formed in the housing configured to be connected to at least one of the indwelling leads; and electronics within the housing and operably connected to the at least one terminal so as to be able to receive signals from the at least one indwelling lead, evaluate the received signals, and selectively deliver electrical stimulation pulses thereto.

2. The system of claim 1 wherein the wand is in wired communication with the programmer.

3. The system of claim 1 wherein the wand is in wireless communication with the programmer.

4. The system of claim 3 wherein the wireless communication comprises RF communication.

5. The system of claim 1, wherein the telemetry wand further comprises a selector such that a user may select between operation of the telemetry wand for telemetric communication with the implantable device with the programmer or as the pacing system analyzer for the at least one indwelling lead.

6. The system of claim 1 wherein the telemetry wand electronics include operational software operable with the operating software of the physician programmer such that the physician programmer, in combination with the telemetry wand, can be selectively operated in a programmer mode or a pacing system analyzer mode.

7. The system of claim 1 further comprising a telemetry cable and wherein the communication between the telemetry wand and the programmer is via the telemetry cable.

8. The system of claim 1 wherein the telemetry wand further comprises a display.

9. The system of claim 8 wherein the telemetry wand electronics is operable in a pacing system analyzer (PSA) mode and the display displays data related to the PSA operation of the wand.

10. The system of claim 9, wherein the display also displays data related to communication with the implantable device.

11. The system of claim 8 wherein:
the telemetry wand operates in a pacing system analyzer (PSA) mode;
the programmer comprises a display; and
the telemetry wand and the programmer each display at least one of data related to communication with the implantable device and data related to the PSA operation of the wand.

12. The system of claim 1 wherein the telemetry wand electronics are operably connected to the at least one terminal under control of software resident within the housing.

13. The system of claim 1 wherein the telemetry wand electronics are operable to program the pacing/sensing electronics in an implantable device through the telemetry circuitry.

14. A telemetry wand for communication with a programmer, an implantable medical device including a programmable microcontroller, and with one or more indwelling leads, the telemetry wand comprising:
a housing;
telemetry circuitry within the housing that is operative to communicate with the implantable medical device and with the programmer, wherein the communication between the telemetry circuitry and the implantable medical device is wireless
at least one terminal formed in the housing configured to be connected to at least one of the indwelling leads; and
electronics within the housing that are operably connected to the at least one terminal to receive signals from the at least one indwelling lead, evaluate the received signals, and selectively deliver electrical stimulation pulses thereto.

15. The telemetry wand of claim 14, further comprising a display operative to display at least a portion of data communicated thereto from the implantable medical device.

16. The telemetry wand of claim 15, wherein the programmer comprises a display and wherein the telemetry wand and the programmer each display at least a portion of the data communicated from the implantable medical device.

17. The telemetry wand of claim 14 wherein the electronics are operably connected to the at least one terminal under control of software resident within the housing.

18. The telemetry wand of claim 14 wherein the electronics are operable to program the microcontroller in an implantable device through the telemetry circuitry.

19. A telemetry wand comprising:
means for facilitating communication with a programmer;
means for facilitating wireless communication with an implantable medical device;
means for facilitating wire receipt of signals from at least one indwelling lead;
means for evaluating the received signals; and
means for selectively delivering electrical stimulation pulses to the at least one indwelling lead.

* * * * *